US012642921B2

(12) United States Patent
Shi et al.

(10) Patent No.: US 12,642,921 B2
(45) Date of Patent: Jun. 2, 2026

(54) ATOMIZING STRUCTURE AND ATOMIZER

(71) Applicant: GUANGZHOU NEWLIFE NEW MATERIAL CO., LTD, Guangzhou (CN)

(72) Inventors: Donghuai Shi, Guangzhou (CN); Keqiang Wang, Guangzhou (CN); Heping Du, Guangzhou (CN); Xiaoming Wang, Guangzhou (CN)

(73) Assignee: GUANGZHOU NEWLIFE NEW MATERIAL CO., LTD., Guangzhou (CN)

( * ) Notice: Subject to any disclaimer, the term of this patent is extended or adjusted under 35 U.S.C. 154(b) by 525 days.

(21) Appl. No.: 18/304,607

(22) Filed: Apr. 21, 2023

(65) Prior Publication Data

US 2023/0347076 A1 Nov. 2, 2023

(30) Foreign Application Priority Data

Apr. 27, 2022 (CN) .......................... 202221013374.3

(51) Int. Cl.
A61M 11/04 (2006.01)
A24F 40/10 (2020.01)
(Continued)

(52) U.S. Cl.
CPC ........... A61M 11/042 (2014.02); A24F 40/10 (2020.01); A24F 40/46 (2020.01); H05B 3/48 (2013.01); H05B 2203/021 (2013.01)

(58) Field of Classification Search
CPC ............... H05B 3/48; H05B 2203/021; A61M 2205/0211; A61M 11/042; A61M 11/041; (Continued)

(56) References Cited

U.S. PATENT DOCUMENTS

2018/0020728 A1* 1/2018 Alarcon ................ G01F 1/6888
392/404
2018/0132531 A1* 5/2018 Sur .................... H01M 10/0525
(Continued)

FOREIGN PATENT DOCUMENTS

WO WO-2021258808 A1 * 12/2021 ............. A24F 40/46

OTHER PUBLICATIONS

Machine translation of written description and claims for WO2021258808A1 via google patents (Year: 2021).*

*Primary Examiner* — Bradley H Philips
*Assistant Examiner* — Tyler A Raubenstraw
(74) *Attorney, Agent, or Firm* — Vivacqua Crane, PLLC

(57) ABSTRACT
An atomizing structure and an atomizer are disclosed. The atomizing structure includes a ceramic part, a heating part and a shell. The heating part is connected with the ceramic part. The ceramic part is arranged in the shell, a side wall of the shell is provided with a liquid inlet region, and the liquid inlet region extends through the side wall of the shell. An annular cavity is arranged between an inner wall of the shell and an outer wall of the ceramic part, the annular cavity is arranged around the outer wall of the ceramic part, an atomized liquid is capable of entering the annular cavity through the liquid inlet region, and the atomized liquid in the annular cavity is capable of entering the ceramic part through pores in the ceramic part.

12 Claims, 5 Drawing Sheets

(51) Int. Cl.
    *A24F 40/46*      (2020.01)
    *H05B 3/48*      (2006.01)

(58) Field of Classification Search
    CPC ......... A61M 11/04; A24F 40/10; A24F 40/42;
                         A24F 40/44; A24F 40/46
    See application file for complete search history.

(56)                References Cited

U.S. PATENT DOCUMENTS

| | | | |
|---|---|---|---|
| 2018/0177957 A1* | 6/2018 | Streeter | A61M 35/003 |
| 2018/0296777 A1* | 10/2018 | Terry | A61M 11/041 |
| 2019/0054261 A1* | 2/2019 | Banoun | A61M 15/08 |
| 2019/0166906 A1* | 6/2019 | Balder | A24F 1/32 |
| 2019/0255267 A1* | 8/2019 | Lindars | A61K 9/007 |
| 2019/0297953 A1* | 10/2019 | Qiu | A61M 11/042 |
| 2020/0077710 A1* | 3/2020 | Volodarsky | A61M 15/06 |
| 2020/0086067 A1* | 3/2020 | Li | A61M 11/042 |
| 2020/0154784 A1* | 5/2020 | Sebastian | A24B 15/167 |
| 2020/0187560 A1* | 6/2020 | Trzecieski | A24F 40/44 |
| 2020/0214361 A1* | 7/2020 | Zhao | H05B 3/06 |
| 2020/0222642 A1* | 7/2020 | Trzecieski | H05B 3/46 |
| 2020/0229511 A1* | 7/2020 | Wang | A24F 40/44 |
| 2022/0287365 A1* | 9/2022 | Alsayar | H05B 3/18 |
| 2023/0339818 A1* | 10/2023 | Li | C04B 35/453 |
| 2024/0023203 A1* | 1/2024 | Wang | A24F 40/10 |
| 2024/0122253 A1* | 4/2024 | Courbat | H05B 6/108 |

* cited by examiner

ATOMIZING STRUCTURE AND ATOMIZER

CROSS-REFERENCE TO RELATED APPLICATION

This application is based on and claims the benefit of priority from Chinese Patent Application No. 202221013374.3, filed on 27 Apr. 2022, the entirety of which is incorporated by reference herein.

TECHNICAL FIELD

The disclosure relates to the technical field of atomizers, and particularly to an atomizing structure and an atomizer.

BACKGROUND

Medicine liquid is vaporized after being heated and then converted into steam, which is one of working methods of the existing atomizers. The medicine liquid enters a surface of a heating structure through pores of a porous structure, and after the heating structure is electrified, the medicine liquid is heated and vaporized quickly to form tiny medicine liquid particles. At present, common atomizers in the market generally have the problems of uneven and insufficient infiltration of atomized liquid, uneven atomization, low atomization efficiency, complicated assembly steps, and easy local overheating, which leads to decomposition or high-temperature chemical reaction due to excessive local temperature of the medicine liquid.

SUMMARY

In order to solve at least one of the above technical problems, the disclosure provides an atomizing structure and an atomizer, and the following technical solution is used.

The atomizer provided by the disclosure comprises the atomizing structure.

The atomizing structure provided by the disclosure comprises a ceramic part, a heating part and a shell, wherein the heating part is connected with the ceramic part; and the ceramic part is arranged in the shell, a side wall of the shell is provided with a liquid inlet region extending through the side wall of the shell; wherein, an annular cavity is arranged between an inner wall of the shell and an outer wall of the ceramic part, the annular cavity is arranged around the outer wall of the ceramic part, an atomized liquid is capable of entering the annular cavity through the liquid inlet region, and the atomized liquid in the annular cavity is capable of entering the ceramic part through pores in the ceramic part.

In some embodiments of the disclosure, the ceramic part surrounds and forms an atomizing region, the atomizing region is provided with a gas dissipation channel, and the heating part is arranged on a side wall of the atomizing region.

In some embodiments of the disclosure, the heating part is embedded in the ceramic part.

In some embodiments of the disclosure, the heating part is provided with a plurality of grid structures.

In some embodiments of the disclosure, the heating part is set as a heating mesh.

In some embodiments of the disclosure, the ceramic part is provided with a protruding structure, the protruding structure is arranged between the inner wall of the shell and the outer wall of the ceramic part to form the annular cavity between the inner wall of the shell and the outer wall of the ceramic part.

In some embodiments of the disclosure, the protruding structure is set as an annular structure, two ends of the ceramic part are respectively provided with the annular structure, and the annular structure is arranged between the outer wall of the ceramic part and the inner wall of the shell to form the annular cavity between the inner wall of the shell and the outer wall of the ceramic part.

In some embodiments of the disclosure, the ceramic part is set to be in a cylindrical shape, and the annular structure is set as a circular annular structure; or, the ceramic part is set to be in a prism shape, and the annular structure is set as a polygonal annular structure.

In some embodiments of the disclosure, the atomizing structure comprises a conductive member, and the conductive member is connected with the heating part.

In some embodiments of the disclosure, a porosity of the ceramic part is 30% to 80%.

In some embodiments of the disclosure, a pore size of the ceramic part is 5 μm to 200 μm.

Embodiments of the disclosure have at least the following beneficial effects. In the atomizing structure, the annular cavity is designed to be formed between the outer wall of the ceramic part and the inner wall of the shell, the atomized liquid enters the annular cavity, the atomized liquid is accumulated in the annular cavity, and a space of the annular cavity surrounds the outer wall of the ceramic part, so that a contact area between the atomized liquid and the ceramic part can be increased, and the atomized liquid is promoted to fully infiltrate into the ceramic part, thus improving an atomization efficiency. The disclosure can be widely used in the technical field of atomizers.

BRIEF DESCRIPTION OF THE DRAWINGS

The above and/or additional aspects and advantages of the disclosure will be apparent and easily understood from descriptions of embodiments with reference to the following drawings.

DETAILED DESCRIPTION

Figure 1:
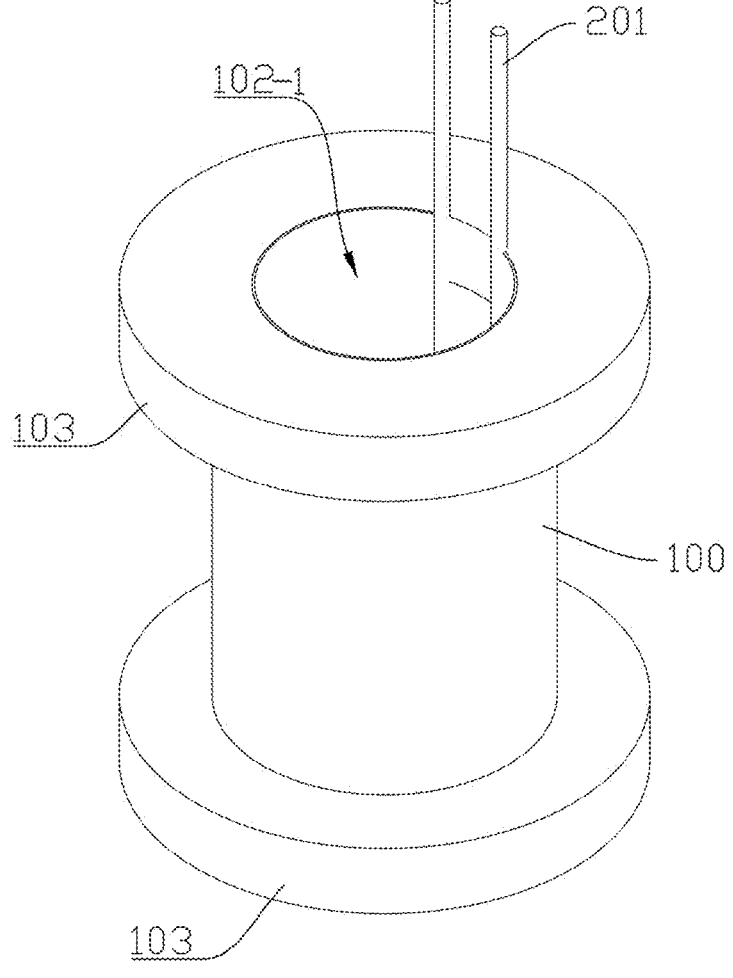
FIG. 1 is a structural diagram of a ceramic part, in which the ceramic part is provided with an annular structure, a heating part is embedded in the ceramic part, and the heating part is connected with a conductive member.
Figure 2:
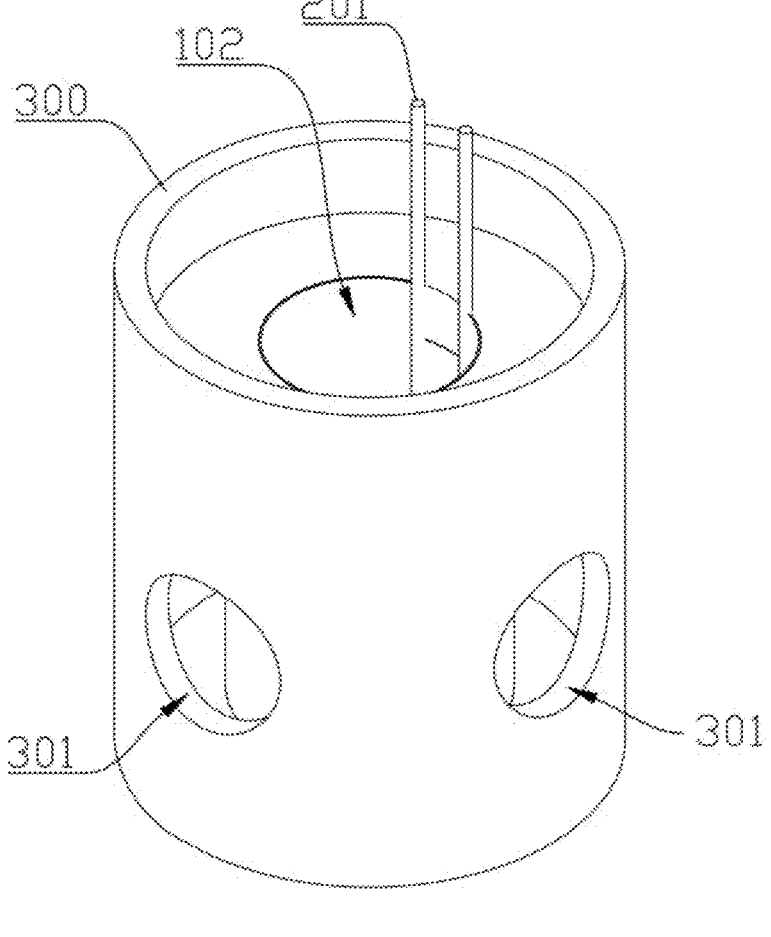
FIG. 2 is a structural diagram of an atomizing structure.
Figure 3:
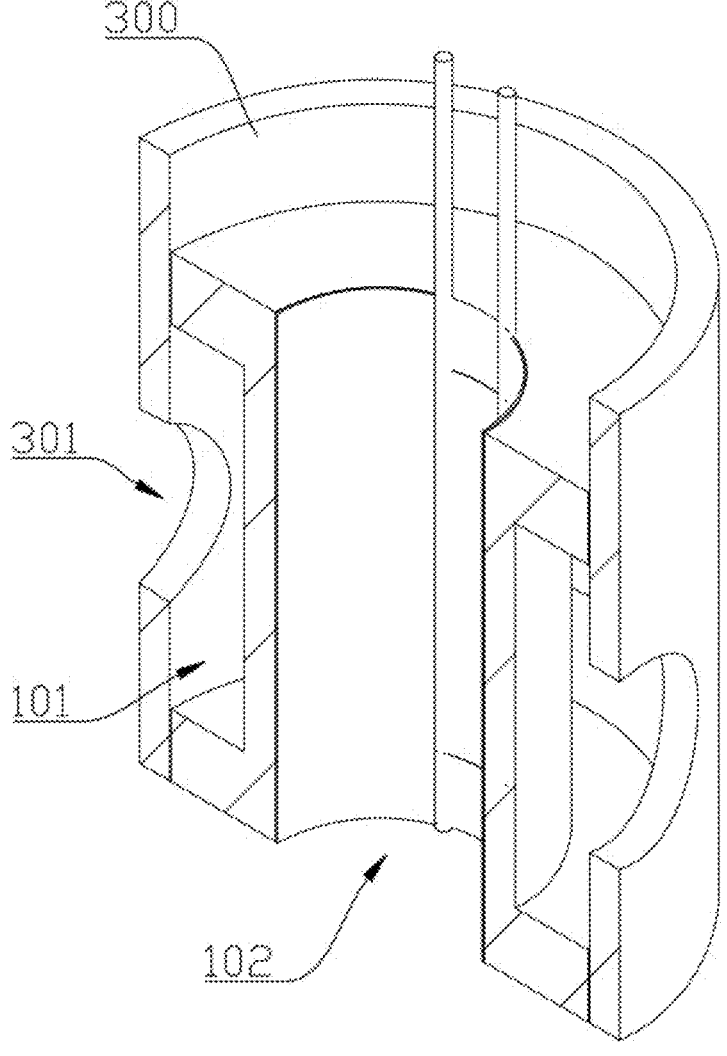
FIG. 3 is a sectional view of the atomizing structure.
Figure 4:
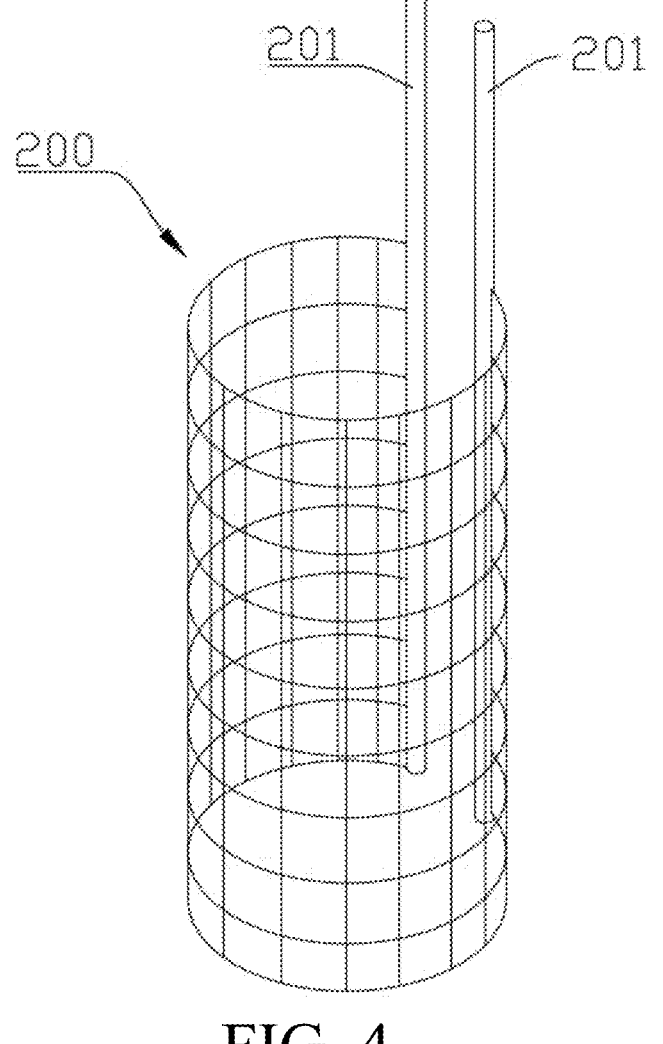
FIG. 4 is a structural diagram of the heating part, in which the heating part is set as a heating mesh, and the heating part is connected with the conductive member.
Figure 5:
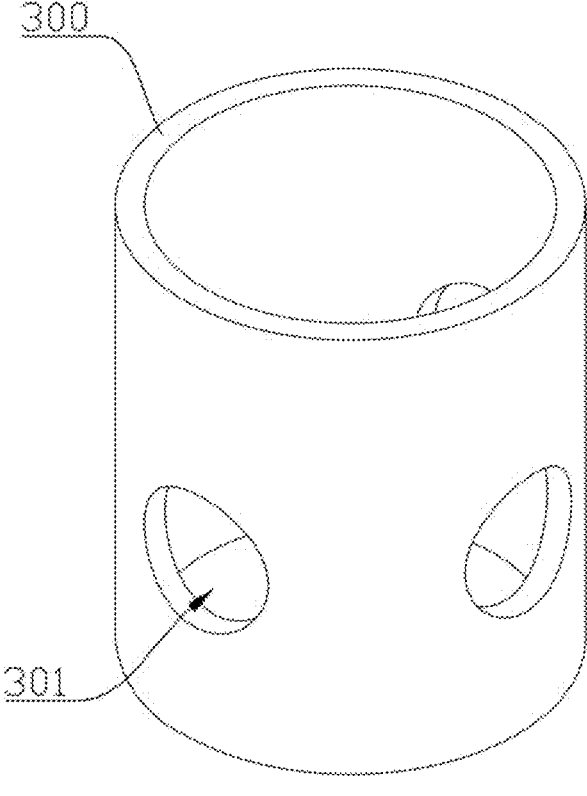
FIG. 5 is a structural diagram of a shell.

Embodiments of the disclosure will be described in detail hereinafter with reference to FIG. 1 to FIG. 5, and examples of the embodiments are shown in the drawings, wherein the same or similar reference numerals throughout the drawings denote the same or similar elements or elements having the same or similar functions. The embodiments described hereinafter with reference to the drawings are exemplary, and are only used to explain the disclosure, but should not be understood as limiting the disclosure.

In the description of the disclosure, it should be understood that the orientation or position relationship indicated by the terms "center", "middle", "longitudinal", "transverse", "length", "width", "thickness", "up", "down", "front", "rear", "left", "right", "vertical", "horizontal", "top", "bottom", "inside", "outside", "axial", "radial", "circumferential", and the like is based on the orientation or position relationship shown in the drawings, it is only for the convenience of description of the disclosure and simplification of the description, and it is not to indicate or imply that the indicated device or element must have a specific orientation, and be constructed and operated in a specific orientation. Therefore, the terms should not be understood as limiting the disclosure. The features defined by "first" and "second" are used to distinguish between feature names, rather than having special meanings. In addition, the features defined by "first" and "second" may explicitly or implicitly comprise one or more of the features. In the description of the disclosure, unless otherwise specified, the term "multiple" refers to being two or more.

In the description of the disclosure, it should be noted that the terms "installation", "connected" and "connection" should be understood in a broad sense unless otherwise specified and defined. For example, they may be fixed connection, removable connection or integrated connection; may be mechanical connection or electrical connection; and may be direct connection, or indirect connection through an intermediate medium, and connection inside two elements. The specific meanings of the above terms in the disclosure may be understood in a specific case by those of ordinary skills in the art.

The disclosure relates to an atomizer, the atomizer is capable of vaporizing an atomized liquid by heating to form steam, thus achieving an atomization effect. The atomizer may be used in fields requiring atomized steam, such as medical atomization and beauty atomization. Certainly, the atomizer may also be applied in other occasions requiring the atomized steam. The atomizer comprises an atomizing structure, the atomizing structure is arranged in the atomizer, and the atomizing structure can sever as an atomizing core.

It can be understood that the atomizer is provided with an exhaust structure, and specifically, the exhaust structure is provided as an exhaust plate with a plurality of exhaust holes. Certainly, as an alternative solution, the exhaust structure may also be designed as a gas nozzle.

In some examples, the atomizer is provided with a power supply module, the power supply module is capable of supplying power to the atomizing structure, and the power supply module is set as a lithium battery or the power supply module is set as a power adapter capable of being plugged into a power supply.

In some examples, the atomizer is provided with a liquid storage device capable of storing the atomized liquid, and the liquid storage device provides the atomized liquid to the atomizing structure through a liquid conveying channel. Certainly, it can be understood that, in some examples, an alternative design is that the atomizer is not provided with the liquid storage device, but is externally connected with the liquid storage device through a liquid conveying pipe.

Other structures and operations of the atomizer have been recorded in the related arts for those of ordinary skills in the art and will not be described in detail herein. A structure of the atomizing structure will be introduced hereinafter.

The disclosure relates to the atomizing structure, and the atomizing structure is capable of vaporizing the atomized liquid by heating. Specifically, the atomizing structure comprises a ceramic part 100 and a heating part 200. The heating part 200 is connected with the ceramic part 100, the atomized liquid is capable of infiltrating into the ceramic part 100, the heating part 200 generates heat by electric heating, and the heat is capable of being conducted to the ceramic part 100, so that the atomized liquid in the ceramic part 100 is vaporized by heating.

It can be understood that the ceramic part 100 has a porous structure, and the atomized liquid is capable of infiltrating into pores in the ceramic part 100. Specifically, the ceramic part 100 is made of at least one of aluminium oxide, zirconium oxide, silicon carbide, silicon dioxide or diatomite. In some examples, a porosity of the ceramic part 100 is designed to be 30% to 80%. In some examples, a pore size of the ceramic part 100 is designed to be 5 $\mu m$ to 200 $\mu m$.

With reference to the drawings, the atomizing structure comprises a shell 300. The ceramic part 100 is arranged in the shell 300, a joint between the ceramic part 100 and the shell 300 is sealed, a side wall of the shell 300 is provided with a liquid inlet region 301, and the liquid inlet region 301 extends through the side wall of the shell 300. It can be understood that the atomized liquid is capable of infiltrating into the ceramic part 100 after passing through the liquid inlet region 301.

Specifically, the liquid inlet region 301 is set as a through hole penetrating through the side wall of the shell 300. With reference to the drawings, there are through holes in multiple positions on the side wall of the shell 300 to form a plurality of liquid inlet regions 301, so that the atomized liquid is capable of entering the shell 300 from the multiple positions, thus increasing the atomized liquid in the atomizing structure.

In some examples, the ceramic part 100 is set to be in a cylindrical shape, the side wall of the shell 300 is arranged around the ceramic part 100, and the side wall of the shell 300 is provided with the plurality of liquid inlet regions 301 in different directions, so that the atomized liquid is capable of entering the shell 300 from the directions.

Further, an annular cavity 101 is arranged between an inner wall of the shell 300 and an outer wall of the ceramic part 100, the annular cavity 101 is arranged around the outer wall of the ceramic part 101, and the annular cavity 101 is capable of being used as a container of the atomized liquid. Specifically, the atomized liquid is capable of entering the annular cavity 101 through the liquid inlet region 301, and the atomized liquid in the annular cavity 101 is capable of entering the ceramic part 100 through the pores in the ceramic part 100. It can be understood that, in this case, more atomized liquid is capable of being accumulated in the annular cavity 101, so that a contact area between the atomized liquid and the ceramic part 100 is increased, which is helpful for the atomized liquid to fully infiltrate into the pores in the ceramic part 100, thus preventing the heating part 200 from dry burning.

The ceramic part 100 is provided with a protruding structure. Specifically, the protruding structure protrudes from the outer wall of the ceramic part 100, and the protruding structure is capable of abutting against the inner wall of the shell 300. It can be understood that the protruding structure is arranged between the inner wall of the shell 300 and the outer wall of the ceramic part, so that the annular cavity 101 is formed between the outer wall of the ceramic part 100 and the inner wall of the shell 300, and a space formed by the annular cavity 101 is a continuous cavity between the outer wall of the ceramic part 100 and the inner wall of the shell 300.

Specifically, the protruding structure is set as an annular structure 103, and the annular structure 103 is arranged along a circumferential direction of the outer wall of the ceramic part 100. Further, two ends of the ceramic part 100 are respectively provided with the annular structure 103, and the annular structure 103 is arranged between the outer wall of the ceramic part 100 and the inner wall of the shell 300 to form the annular cavity 101 between the inner wall of the shell 300 and the outer wall of the ceramic part 100. It can be understood that the annular cavity 101 is a continuous annular space surrounding the outer wall of the ceramic part 100, so that the atomized liquid can fully infiltrate into the ceramic part 100, thus ensuring a continuous, fine, uniform and full atomization effect.

With reference to the drawings, the annular structure 103 facilitates sealing with the inner wall of the shell 300, and a space formed by the annular structures 103 at two ends, the outer wall of the ceramic part 100 and the inner wall of the shell 300 forms the annular cavity 101. In this case, the outer wall of the ceramic part 100 and a wall surface of the annular structure 103 are both capable of being contacted with the atomized liquid, so that the contact area between the atomized liquid and the ceramic part 100 is further effectively increased, thus improving the atomization efficiency.

It can be understood that the ceramic part 100 is integrally molded by sintering, so that two ends of the ceramic part 100 are designed to be provided with the integrally molded annular structure 103. With reference to the drawings, the ceramic part 100 has an "I-shaped" structure, and this shape can also effectively improve a structural strength of the ceramic part 100.

Further, the inner wall of the shell 300 is in sealing connection with the annular structure 103 to prevent the atomized liquid from leaking. Specifically, a sealing ring may be arranged between the inner wall of the shell 300 and the annular structure 103, or an adhesive may be used for adhesion, fixation and sealing.

In some examples, when the ceramic part 100 is set to be in the cylindrical shape, the annular structure 103 is set as a circular annular structure, and correspondingly, the inner wall of the shell 300 is set as a circular annular wall surface. Certainly, as an alternative solution: in some examples, the ceramic part 100 may also be set to be in a prism shape, and correspondingly, the annular structure 103 is set as a polygonal annular structure. It can be understood that the inner wall of the shell 300 is set as a polygonal wall surface.

As an embodiment, the ceramic part 100 surrounds and forms an atomizing region 102, and the atomizing region 102 is provided with a gas dissipation channel 102-1. The atomized liquid subjected to vaporization is dissipated from the ceramic part 100 to the atomizing region 102, and then dissipated from the atomizing region 102 to the exhaust structure of the atomizer. Specifically, a hollow cavity is formed in the ceramic part 100, which is used as the atomizing region 102 of the ceramic part 100. Further, an end portion of the hollow cavity of the ceramic part 100 is open, which is used as the gas dissipation channel 102-1 of the atomizing region 102.

The heating part 200 is arranged on a side wall of the atomizing region 102. With reference to the drawings, the side wall on which the heating part 200 is located is an inner wall of the hollow cavity of the ceramic part 100, and the heating part 200 heats the atomized liquid in a process that the atomized liquid infiltrates into the inner wall of the ceramic part 100 from the outer wall of the ceramic part 100. It can be understood that, in this case, there is fully infiltrated atomized liquid in the ceramic part 100 to ensure that heat generated by the heating part 200 is capable of being fully used for atomization, thus improving heating efficiency and atomization uniformity.

In some examples, the heating part 200 is embedded in the ceramic part 100 to form an integrated structure of the heating part 200 and the ceramic part 100, which can promote heat conduction, reduce assembly steps of the atomizing structure, and realize miniaturization of the atomizing structure. Specifically, during sintering and molding of the ceramic part 100, the heating part 200 is placed in a mold, and after finishing high-temperature sintering, the heating part 200 is embedded in the ceramic part 100.

It can be understood that when the ceramic part 100 is provided with the atomizing region 102, the heating part 200 is embedded in the side wall of the atomizing region 102. Specifically, the heating part 200 is embedded in the inner wall of the hollow cavity of the ceramic part 100, so that the heat generated by the heating part 200 is capable of being fully conducted to the ceramic part 100, thus improving heating efficiency.

Certainly, as an alternative solution: in some examples, if the ceramic part 100 is not provided with the hollow cavity, the heating part 200 is embedded in the ceramic part 100, or the heating part 200 is embedded in a surface of the ceramic part 100.

As an embodiment, the heating part 200 is provided with a plurality of grid structures, so that the heating part 200 is capable of being fully contacted with the ceramic part 100, and heat conduction can be enhanced. It can be understood that when the heating part 200 is embedded in the ceramic part 100, the grid structure of the heating part 200 can more easily forming an embedded structure into the side wall of the ceramic part 100, which is more convenient for sintering and molding of the ceramic part 100, thus improving a connection strength between the heating part 200 and the ceramic part 100.

With reference to the drawings, the heating part 200 is set as a heating mesh, or a heating sheet with a plurality of grid structures formed by hollowing out. The heating part 200 is arranged in the atomizing region along a circumferential direction of the side wall, and after the heating part 200 is embedded in the ceramic part 100, the heating part 200 is formed into the cylindrical shape, and the heat generated by the heating part 200 is capable of being uniformly conducted to all positions on the ceramic part 100, thus realizing large-area heating and miniaturization of the atomizing structure.

In the related art, a spiral heating wire is used for heat generation, and the heating wire has a small heating area, resulting in that the atomization efficiency is low, and it is easy to lead to local high temperature. However, the heating part 200 of the disclosure is set as the heating mesh, which can increase the heating area and improve the atomization efficiency, and grids of the heating mesh are evenly distributed, leading to uniform heating and atomization, and a good atomization effect.

It can be understood that the heating part 200 is made of a metal material, and specifically, the heating part 200 is made of Fe—Cr—Al alloy or Ni—Cr alloy.

A power supply module of the atomizer is capable of supplying power to the atomizing structure. It can be understood that the atomizing structure comprises a conductive member 201, the conductive member 201 is connected with the heating part 200, the conductive member 201 is connected with the power supply module of the atomizer, and the conductive member 201 conducts electricity for the heating part 200. With reference to the drawings, two conductive members 201 are provided, and the two conductive members 201 are respectively connected with a positive electrode and a negative electrode of the power supply module.

Specifically, the conductive member 201 is set as a wire, the conductive member 201 is made of nickel alloy, copper alloy or iron alloy, and the conductive member 201 is welded and fixed with the heating part 200. Certainly, as an alternative solution, the conductive member 201 may also be set as a pin.

In the descriptions of the specification, the descriptions with reference to the terms "one embodiment", "some instances", "some embodiments", "illustrative embodiment", "example", "specific example" or "some examples", etc., refer to that specific features, structures, materials, or characteristics described with reference to the embodiments or examples are included in at least one embodiment or example of the disclosure. In the specification, the schematic representation of the above terms does not necessarily mean the same embodiment or example. Moreover, the specific features, structures, materials or characteristics described may be combined in any one or more embodiments or examples in a suitable manner.

The embodiments of the disclosure are described in detail with reference to the drawings above, but the disclosure is not limited to the above embodiments, and various changes may also be made within the knowledge scope of those of ordinary skills in the art without departing from the purpose of the disclosure.

In the descriptions of the disclosure, if "," appears in the patent title, it means the relationship of "and" instead of "or". For example, when the patent tile is "an A, B", it indicates that the content required to be protected by the disclosure is: the technical solution with the title of A and the technical solution with the title of B.

We claim:

1. An atomizing structure, comprising: a ceramic part; a heating part, wherein the heating part is connected with the ceramic part; and a shell, wherein the ceramic part is arranged in the shell, a side wall of the shell is provided with a liquid inlet region extending through the side wall of the shell; wherein, an annular cavity is arranged between an inner wall of the shell and an outer wall of the ceramic part, the annular cavity is arranged around the outer wall of the ceramic part, an atomized liquid is capable of entering the annular cavity through the liquid inlet region, and the atomized liquid in the annular cavity is capable of entering the ceramic part through pores in the ceramic part; wherein the ceramic part is integrally molded by sintering; wherein the heating part is embedded in the ceramic part through: during sintering and molding of the ceramic part, placing the heating part in a mold used for forming the ceramic part of the atomizing structure, and after finishing sintering, the heating part is embedded in the ceramic part, thereby forming an integrated structure of the heating part and the ceramic part;

wherein the ceramic part is provided with a protruding structure, the protruding structure is arranged between the inner wall of the shell and the outer wall of the ceramic part to form the annular cavity between the inner wall of the shell and the outer wall of the ceramic part; and wherein the protruding structure is set as an annular structure, the ceramic part is set as a cylinder having an annular first sidewall and two first bottom surfaces, the two first bottom surfaces located at two ends of the ceramic part are respectively provided with the annular structure, and the annular structure is arranged between the outer wall of the ceramic part and the inner wall of the shell to form the annular cavity between the inner wall of the shell and the outer wall of the ceramic part; wherein the annular structure is integrally molded with the ceramic part; and wherein: the annular structure is set as a circular annular structure having an annular second sidewall and two second bottom surfaces; or, the ceramic part is set to be in a prism shape, and the annular structure is set as a polygonal annular structure having a polygonal annular second sidewall and two second bottom surfaces; wherein the two first bottom surfaces of the ceramic part contact the second bottom surfaces of the annular structure, and wherein the first bottom surface and the second bottom surface share a common center, a diameter of the first bottom surfaces is smaller than a diameter of the second bottom surface, such that the ceramic part has an I-shaped structure.

2. The atomizing structure according to claim 1, wherein the ceramic part surrounds and forms an atomizing region, an end portion of a hollow cavity of the ceramic part is open, which is used as a gas dissipation channel of the atomizing region, and the heating part is arranged on a side wall of the atomizing region.

3. The atomizing structure according to claim 1, wherein the heating part is provided with a plurality of grid structures.

4. The atomizing structure according to claim 3, wherein the heating part is set as a heating mesh.

5. The atomizing structure according to claim 1, wherein the atomizing structure comprises a conductive member, and the conductive member is connected with the heating part.

6. The atomizing structure according to claim 1, wherein a porosity of the ceramic part is 30% to 80%.

7. The atomizing structure according to claim 1, wherein a pore size of the ceramic part is 5 μm to 200 μm.

8. An atomizer, comprising an atomizing structure comprising: a ceramic part; a heating part, wherein the heating part is connected with the ceramic part; and a shell, wherein the ceramic part is arranged in the shell, a side wall of the shell is provided with a liquid inlet region extending through the side wall of the shell; wherein, an annular cavity is arranged between an inner wall of the shell and an outer wall of the ceramic part, the annular cavity is arranged around the outer wall of the ceramic part, an atomized liquid is capable of entering the annular cavity through the liquid inlet region, and the atomized liquid in the annular cavity is capable of entering the ceramic part through pores in the ceramic part; wherein the ceramic part is integrally molded by sintering; wherein the heating part is embedded in the ceramic part through: during sintering and molding of the ceramic part, placing the heating part in a mold used for forming the ceramic part of the atomizing structure, and after finishing sintering, the heating part is embedded in the ceramic part, thereby forming an integrated structure of the heating part and the ceramic part;

wherein the ceramic part is provided with a protruding structure, the protruding structure is arranged between the inner wall of the shell and the outer wall of the ceramic part to form the annular cavity between the inner wall of the shell and the outer wall of the ceramic part; and wherein the protruding structure is set as an annular structure, the ceramic part is set as a cylinder having an annular first sidewall and two first bottom surfaces, the two first bottom surfaces located at two ends of the ceramic part are respectively provided with the annular structure, and the annular structure is arranged between the outer wall of the ceramic part and the inner wall of the shell to form the annular cavity between the inner wall of the shell and the outer wall of the ceramic part; wherein the annular structure is integrally molded with the ceramic part; and wherein: the annular structure is set as a circular annular structure having an annular second sidewall and two second bottom surfaces; or, the ceramic part is set to be in a prism shape, and the annular structure is set as a polygonal annular structure having a polygonal annular second sidewall and two second bottom surfaces; wherein the two first bottom surfaces of the ceramic part contact the second bottom surfaces of the annular structure, and wherein the first bottom surface and the second bottom surface share a common center, a diameter of the first bottom surfaces is smaller than a diameter of the second bottom surface, such that the ceramic part has an I-shaped structure.

9. The atomizer according to claim 8, wherein the ceramic part surrounds and forms an atomizing region, an end portion of a hollow cavity of the ceramic part is open, which is used as a gas dissipation channel of the atomizing region, and the heating part is arranged on a side wall of the atomizing region.

10. The atomizer according to claim 8, wherein the heating part is provided with a plurality of grid structures.

11. The atomizer according to claim 10, wherein the heating part is set as a heating mesh.

12. The atomizer according to claim 8, wherein the atomizing structure comprises a conductive member, and the conductive member is connected with the heating part.

* * * * *